Figure 1:
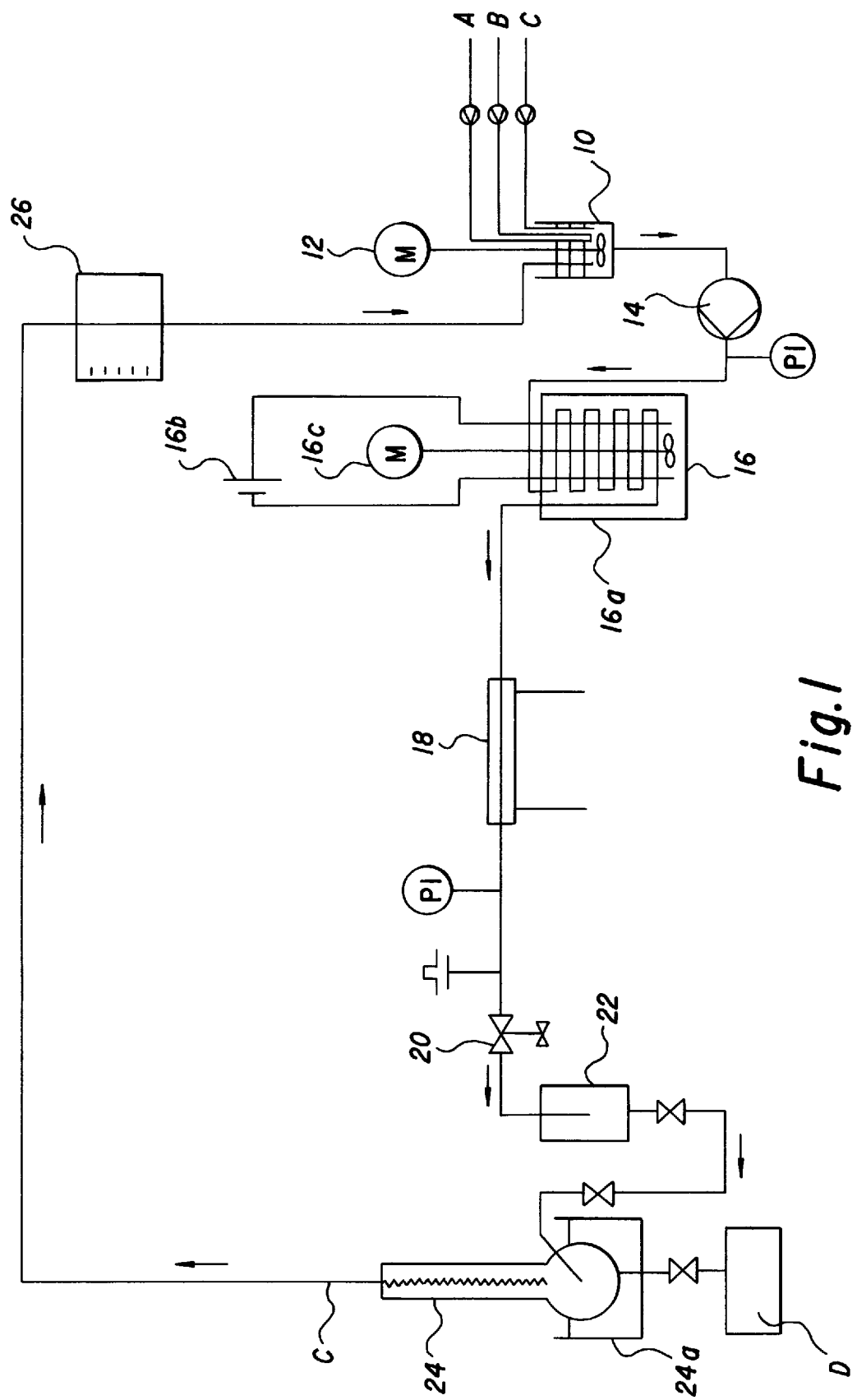

United States Patent [19]
Gnann et al.

[11] Patent Number: 5,831,134
[45] Date of Patent: *Nov. 3, 1998

[54] CONTINUOUS PRODUCTION PROCESS OF TERTIARY ALCOHOLS BY RADICAL ADDITION OF SECONDARY ALCOHOLS TO ALKENES

[75] Inventors: Michael Gnann, Grosshesselohe; Maria Eckert, Eurasburg; Robert Rieth, deceased, late of Berg, by Johanna Tojek-Rieth, heir; Werner Eberhard Wilhelm Rieth, heir; Emma Marianne Christine Rieth, heir, both of Besigheim, all of Germany

[73] Assignee: Peroxid-Chemie GmbH, Hollriegelskreuth, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 532,577
[22] PCT Filed: Apr. 19, 1994
[86] PCT No.: PCT/EP94/01214
  § 371 Date: Oct. 25, 1996
  § 102(e) Date: Oct. 25, 1996
[87] PCT Pub. No.: WO94/24078
  PCT Pub. Date: Oct. 27, 1994

[30] Foreign Application Priority Data

Apr. 20, 1993 [DE] Germany .......................... 43 12 815.7

[51] Int. Cl.$^6$ ..................................................... C07C 35/08
[52] U.S. Cl. ......................... 568/822; 568/715; 568/834; 568/852; 568/904; 968/905
[58] Field of Search ................................... 568/904, 905, 568/715, 834, 852, 822

[56] References Cited

PUBLICATIONS

Webster's II New Riverside University Dictionary, 1994.

*Primary Examiner*—Michael L. Shippen
*Attorney, Agent, or Firm*—Nikaido, Marmelstein, Murray & Oram LLP

[57] ABSTRACT

A process is disclosed for producing tertiary alcohols by radical addition of secondary alcohols to alkenes. The reaction is carried out as a continuous process in the presence of an organic peroxide as a radical initiator and during a mean contact time of the reaction mixture of up to a maximum of 1 hour.

9 Claims, 1 Drawing Sheet

CONTINUOUS PRODUCTION PROCESS OF TERTIARY ALCOHOLS BY RADICAL ADDITION OF SECONDARY ALCOHOLS TO ALKENES

DESCRIPTION

The present invention concerns a new process for the production of tertiary alcohols by radical addition of secondary alcohols to carbon-carbon double bond systems.

The addition of secondary alcohols to alkenes with formation of tertiary alcohols is in principle known in the art.

U.S. Pat. No. 3,352,929 describes the production of condensation products from isopropanol and acetylene compounds. This process can be carried out in two steps, the first step comprising reaction of an acetylene compound with isopropanol to form an alkenol and the second step comprising the addition of a further isopropanol with formation of a saturated tertiary (multivalent) alcohol. This reaction can be carried out in the presence of organic peroxides as a catalyst. According to U.S. Pat No. 3,352,929 (column 5, lines 43–51) only a short reaction period of e.g. 5 minutes is necessary for the first step of the reaction i.e. the addition of a secondary alcohol to a carbon-carbon triple bond whereas a considerably longer reaction period of about two to five hours is required for the second step i.e. the addition of a further molecule of isopropanol to the addition product of the first reaction step having a carbon-carbon double bond.

In addition it is known from "Methoden der organischen Chemie" (Houben-Weyl), Vol. VI/1b, Georg Thieme Verlag Stuttgart, N.Y., 1984, page 654 ff) that tertiary alcohols can be obtained by addition of alcohols (e.g. secondary alcohols such as isopropanol, isobutanol) to alkenes. The reaction is carried out by heating the olefin in excess alcohol (in a molar ratio of olefin to alcohol of 1:10–50) with addition of a dialkyl peroxide as an initiator (10 to 20 mole percent with respect to the olefin) to 110° to 135° C. for a time period of 35 to 40 hours. In this literature reference it is described that higher alcohols are mainly obtained by telomerization while the monomeric addition product is formed only in a relatively low yield.

Thus a serious disadvantage of the reactions described above is that considerable amounts of telomeric or polymeric by-products are formed in the reaction mixture due to the long contact period of the reactants of several hours. A further disadvantage of the processes of the state of the art is the low/space time yield of monomeric addition products due to the long reaction period.

Therefore the object of the present invention was to provide a process for the production of tertiary alcohols by addition of secondary alcohols to alkenes in which the above-mentioned disadvantages can be completely or at least substantially avoided.

The object according to the invention is achieved by a process for the production of tertiary alcohols by radical addition of secondary alcohols to alkenes which is characterized in that the reaction is carried out as a continuous process in the presence of an organic peroxide as a radical initiator and with an average contact time of the reaction mixture of up to a maximum of 1 hour.

It was surprisingly found that by carrying out the reaction continuously according to the present invention a monomeric addition product is obtained in a high space/time yield and with a low amount of polymeric or/and telomeric by-products even with a contact time of the reaction mixture of up to a maximum of 1 hour, preferably up to a maximum of 30 minutes, particularly preferably up to a maximum of 20 minutes.

The production of tertiary alcohols by a radical addition reaction of secondary alcohols to carbon-carbon double bond systems takes place according to the following reaction scheme:

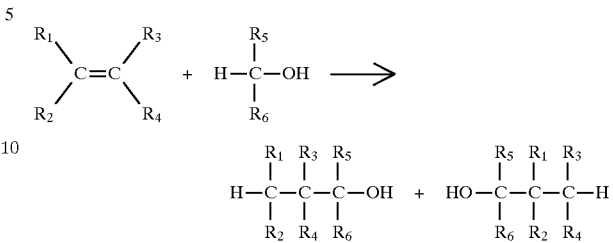

in which $R_1$, $R_2$, $R_3$ and $R_4$ denote hydrogen or alkyl or aryl residues which are substituted if desired and $R_5$ and $R_6$ denote alkyl or aryl residues which are substituted if desired.

The process according to the invention has a broad range of applications since it can be carried out advantageously with a large number of different alkenes and secondary alcohols. Compounds with 2 to 20 C atoms, particularly preferably 4 to 16 C atoms which can if desired carry substituents which do not impair the reaction (e.g. OH groups, O-alkyl groups, aromatic groups) are preferably used as alkenes. Specific examples of particularly preferred alkenes are 2-methyl-3-buten-2-ol, 3-methyl-3-buten-1-ol, 1-tetradecene, 1-dodecene, cyclohexene and α-methylstyrene. The most preferred alkene is 2-methyl-3-buten-2-ol.

Substances with preferably 3 to 14 C atoms, particularly preferably 3 to 10 C atoms are used as a secondary alcohol in the process according to the invention. Furthermore it is preferred that the secondary alcohol is used in an excess of 3 to 50 moles, particularly preferably of 3 to 20 moles alcohol per mole alkene used. Specific examples of preferred secondary alcohols are 2-propanol (isopropanol), 2-butanol, 2-octanol, cyclo-hexanol, 3,3-dimethylbutan-2-ol, 2,6-dimethylheptan-4-ol and 1-phenylethanol. The most preferred alcohol is isopropanol.

The process according to the invention is therefore particularly preferably used for the addition of isopropanol to 2-methyl-3-buten-2-ol in which 2,5-dimethylhexan-2,5-diol is formed as the addition product.

The process according to the invention is in addition carried out in the presence of an organic peroxide as a radical initiator. Preferred examples of organic peroxides are peroxycarboxylic acid esters (e.g. tert.-butylperoxy pivalate, tert.-amylperoxy pivalate), dialkyl peroxides (e.g. di-tert.-butyl peroxide, ditert.-amyl peroxide) and peroxyketals. The amount of radical initiator is preferably 1 to 50 mole percent, particularly preferably 5 to 30 mole percent with respect to the alkene used.

The temperature in the process according to the invention is preferably between 50° and 240° C., particularly preferably between 80° and 200° C. depending on the radical initiator used. When di-tert.-butyl peroxide is used as the initiator, the temperature is preferably between 150° and 200° C. Depending on the alkene used, the reaction can be carried out under normal pressure or under increased pressure. However, it is generally preferred that the reaction be carried out under increased pressure and in a pressure-tube reactor. In such a procedure for the process the pressure can for example be in a range of 5 to 100 bar (500 kPa to 10000 kPa).

In addition it is preferred in the process according to the invention that, after completing the reaction, secondary alcohol be removed continuously from the product mixture (e.g. by distillation) and returned to the reaction mixture.

A diagram of a particularly preferred embodiment of the process according to the invention can be seen in FIG. 1. In this case the reaction partners namely the alkene (A), the radical initiator (B) and the secondary alcohol (C) are led into a mixing vessel 10 which is provided with a stirrer 12 by means of three separate lines. The reaction mixture is led out of the mixing vessel 10 by a pump 14 into a tube reactor 16 which is located in heating bath 16a with a heating rod 16b and stirrer 16c. The contact time of the reaction mixture in the tube reactor is preferably 10 to 20 minutes in this process. Then the mixture is passed through a cooler 18 and a pressure release valve 20 into a receiving vessel 22. The reaction mixture is passed from the receiving vessel 22 to a distillation unit 24 which is equipped with a heating bath 24a. After removing non-reacted secondary alcohol (C) by distillation the reaction product (D) can be isolated there from the distillation residue. The distilled secondary alcohol (C) is collected in a distillation vessel 26 and from there is again added to the mixing vessel 10.

The invention is elucidated further by the following examples.

EXAMPLE 1

2-Methyl-3-buten-2-ol, 2-propanol and di-tert.-butyl peroxide are passed in a molar ratio of 1:10:0.2 into a vessel provided with a stirrer and mixed therein. This reaction mixture is continuously pumped at a pressure of 3000 kPa through the tube coils of a 1000 ml tube reactor. In this process the tube reactor is located in a heating bath heated to 180° C. The flow rate through the tube reactor is set so that the contact time of the reaction mixture in the reactor is ca. 15 minutes (3.8 1/h). The olefin used has completely reacted within this period.

After leaving the reactor, the reaction mixture is cooled and collected via a pressure reducing valve in a collection vessel from which it can be passed into a distillation apparatus. Excess 2-propanol is removed during the subsequent distillation and continuously fed back into the process. The addition product 2,5-dimethyl-hexane-25-diol is present in the distillation residue. 380 g product/h is obtained (purity>97 GC liq.%).

EXAMPLE 2

1-Tetradecene, 2-propanol and di-tert.-butyl peroxide are reacted in a molar ratio of 1:15:0.1 as described in example 1 at a pressure of 3000 kPa. The contact time of the reaction mixture in a reactor that is heated to 175° C. is ca. 20 minutes. 1-Tetradecene has completely reacted after this time. The addition product 2-methyl-2-hexadecanol is formed with a selectivity of 65% and isolated as described in example 1.

EXAMPLE 3

2-Methyl-3-buten-2-ol, cyclohexanol and di-tert.-butyl peroxide are reacted in a molar ratio of 1:15:0.25 as described in example 1 at a pressure of 2500 kPa. After a reaction period of 15 minutes the 2-methyl-3-buten-2-ol used has already been completely converted. The addition product is isolated from the distillation residue as described in example 1 with a selectivity of 85%.

EXAMPLE 4

2-Methyl-3-buten-2-ol, 2-propanol and tert.-butyl peroxy pivalate (75% solution in aliphates) are reacted in a molar ratio of 1:15:0.3 at 90° C. and a pressure of 500 kPa as described in example 1. After a contact period of 20 minutes of the reaction mixture in a tube reactor 95% of the olefin used has been converted. 2,5-dimethylhexane-2,5-diol is formed with a selectivity of 76%.

It is claimed:

1. Process for the production of tertiary alcohol by addition of one molecule of secondary alcohol to one molecule of alkene, wherein
    the reaction is carried out as a continuous process in the presence of an organic peroxide as a radical initiator, the secondary alcohol being used in a ratio of 3 to 50 moles per mole of the alkene used, and with an average contact time of the reaction mixture of up to a maximum of 1 hour.

2. Process as claimed in claim 1, wherein the reaction is carried out with an average contact time of the reaction mixture of up to a maximum of 30 minutes.

3. Process as claimed in claim 1, wherein an alkene with 2 to 20 C atoms is used.

4. Process as claimed in claim 1, wherein a secondary alcohol with 3 to 14 C atoms is used.

5. Process as claimed in claim 1, wherein peroxycarboxylic acid esters or dialkyl peroxides are used as the radical initiator.

6. Process as claimed in claim 1, wherein the initiator is used in a ratio of 1 to 50 mole percent with respect to the alkene used.

7. Process as claimed in claim 1, wherein the reaction is carried out at a temperature of 50 to 240° C. and under normal pressure or increased pressure.

8. Process as claimed in claim 1; wherein the reaction is carried out in a tube reactor under increased pressure.

9. Process as claimed in claim 1, wherein after carrying out the reaction the product is separated from the reaction mixture and non-reacted secondary alcohol is fed back into the reaction mixture.

* * * * *